US008227207B2

(12) United States Patent
Miguel Castro et al.

(10) Patent No.: US 8,227,207 B2
(45) Date of Patent: Jul. 24, 2012

(54) BIOACTIVE PEPTIDES DERIVED FROM THE PROTEINS OF EGG WHITE BY MEANS OF ENZYMATIC HYDROLYSIS

(75) Inventors: Marta Miguel Castro, Madrid (ES); Rosina Lopez-Alonso Fandiño, Madrid (ES); Maria Isidra Recio Sanchez, Madrid (ES); Maria Mercedes Ramos Gonzalez, Madrid (ES); Amaya Aleixandre De Artiñano, Madrid (ES)

(73) Assignee: Consejo Superior de Investigaciones Cientifcas, Madrid (ES)

(*) Notice: Subject to any disclaimer, the term of this patent is extended or adjusted under 35 U.S.C. 154(b) by 968 days.

(21) Appl. No.: 11/343,263

(22) Filed: Jan. 30, 2006

(65) Prior Publication Data
US 2006/0280804 A1    Dec. 14, 2006

Related U.S. Application Data

(63) Continuation of application No. PCT/ES2004/070059, filed on Jul. 23, 2004.

(51) Int. Cl.
*C07K 1/12* (2006.01)
*C07K 1/14* (2006.01)
*C07K 17/00* (2006.01)
*A61K 38/01* (2006.01)
*C12P 1/00* (2006.01)
*C07K 14/435* (2006.01)
*C07K 14/77* (2006.01)

(52) U.S. Cl. .......... 435/41; 530/362; 530/367; 530/300; 530/343; 530/344; 530/333; 530/334; 435/388

(58) Field of Classification Search .................. None
See application file for complete search history.

(56) References Cited

U.S. PATENT DOCUMENTS

| | | | | |
|---|---|---|---|---|
| 5,470,970 A | * | 11/1995 | Sager et al. | 536/23.5 |
| 5,801,001 A | * | 9/1998 | Sager et al. | 435/7.23 |
| 5,905,023 A | * | 5/1999 | Sager et al. | 435/6 |
| 6,495,344 B1 | * | 12/2002 | Carr et al. | 435/69.1 |
| 6,495,347 B1 | * | 12/2002 | Siegel et al. | 435/69.7 |
| 6,514,941 B1 | | 2/2003 | Tolton, II et al. | |
| 6,657,055 B2 | * | 12/2003 | Siegel et al. | 536/23.72 |
| 7,265,208 B2 | * | 9/2007 | Saxon et al. | 530/387.1 |
| 2003/0050469 A1 | * | 3/2003 | Siegel et al. | 536/23.72 |
| 2003/0082190 A1 | * | 5/2003 | Saxon et al. | 424/178.1 |

FOREIGN PATENT DOCUMENTS

| | | | |
|---|---|---|---|
| JP | 05331190 A | * | 12/1993 |
| JP | 09263597 A | * | 10/1997 |
| JP | 10036394 A | * | 2/1998 |
| WO | WO01/85984 A1 | | 11/2001 |

OTHER PUBLICATIONS

Kitabatake, N., Indo, K., and Doi, E. "Limited Proteolysis of Ovalbumin by Pepsin" J. Agric. Food Chem.,1988,36(3), pp. 417-420.*
T. Takano, Milk derived peptides and hypertension reduction, International Dairy Journal, 1998, 8: 375-381.
K. Suetsuna, H. Ukeda and H. Ochi, Isolation and characterization of free radical scavenging activites peptides derived from casein, Journal of Nutritional Biochemistry, 2000, 11:128-131.
S.G. Rival, S. Fornaroli, C.G. Boeriu and H. J. Wichers, Caseins and casein hydrolysates. I. Lipoxygensase inhibitory properties, Journal of Agricultural and Food Chemistry, 2001, 49: 287-294.
H.M. Chen, K. Muramoto, F. Yamauchi, K. Fujimoto and K. Nokihara. Antioxidative properties of histidine-containing peptides designed from peptide fragments found in the digests of soybean protein, Journal of Agricultural and Food Chemistry, 1998, 46: 49-53.
F. Bonomi, A. Fiocchi, H. Frokiaer, A. Gaiaschi, S. lametti, C. Poesi, P. Poesi, P. Rasmussen, P. Restani and P. Rovere, Reduction of immunoreactivity of bovine beta-lactoglobulin upon combined physical and proteolytic treatment, Journal of Dairy Research, 2003, 70: 51-59.
H. Fujita et al, Classification and antihypertensive activity of angiotensin I-converting enzyme inhibitory peptides derived from food proteins, Journal of Food Science, 2000, 65: 564-569.
H. Fujita et al, LKPNM: a prodrug-type ACE-inhibitory peptide derived from fish protein, Immunopharmacology, 1999, 44: 123-127.
H. Fujita et al, Isolation and characterization of ovokinin, a bradykinin B1 agonist peptide derived from ovalbumin, Peptides, 1995, 16: 785-790.
H. Fujita et al, Potentiation of the antihypertensive activity of orally administered ovokinin, a vasorelaxing peptide derived from albumin, by emulsification in egg phosphatidyl-choline, Bioscience Biotechnology and Biochemistry, 1995, 59: 2344-2345.
N. Matoba et al, A novel anti-hypertensive peptide derived from ovalbumin induces nitric oxide-mediated vasorelaxation in an isolated SHR mesenteric artery, FEBS Letters, 1999, 452:181-184.
N. Matoba et al, Designing potent derivatives of ovokinin (2-7), an anti-hypertensive peptide derived from ovalbumin, Bioscience Biotechnology and Biochemistry, 2001, 65: 736-739.
Y. Yamada et al, Design of a highly potent anti-hypertensive peptide based on ovalbumin (2-7), Bioscience Biotechnology and Biochemistry, 2002, 66: 1213-1217.

(Continued)

*Primary Examiner* — Chris R Tate
*Assistant Examiner* — Aaron J Kosar
(74) *Attorney, Agent, or Firm* — Klauber & Jackson LLC

(57) ABSTRACT

The invention relates to the production of ovoproducts containing bioactive peptides from the egg white subjected to enzymatic treatment. Said peptides have an inhibiting activity of the angiotensin converting enzyme (ACE inhibiting activity) in vitro and/or anti-hypertensive activity in rats and/or antioxidant activity. Said ovoproducts, complete hydrolyzates, the fractions thereof with low molecular weight or their constituent peptides could be used as therapeutic substances with ACE inhibiting activity and/or anti-hypertensive activity and/or anti-oxidant activity, either as functional food products, food additives or ingredients or pharmaceutical products for the treatment and/or prevention of hypertension in all its forms in humans or animals and for the treatment and/or prevention of any disorder associated with hypertension in humans or animals.

6 Claims, 8 Drawing Sheets

OTHER PUBLICATIONS

A. Pihlanto-Lippala et al, Angiotensin-I-converting enzyme inhibitory peptides derived from bovine milk proteins, International dairy Journal, 1998, 8: 325-331.

M. Maeno et al, Identification of an anti-hypertensive peptide from casein hydrolysate produced by a proteinase from *Lactobacillus helveticus* CP790, Journal of Dairy Science, 1996, 79: 1316-1321.

D.W. Cushman et al, Spectrophotometric assay and properties of the angiotensin-converting enzyme of rabbit lung. Biochemical Pharmacology, 1971, 20: 1637-1648.

Y.K. Kim et al, Novel angiotensin-I-converting enzyme inhibitory peptides derived from recombinant human alpha$_{s1}$-casein expressed in *Escherichia coli*, Journal of Dairy Research 1999, 66: 431-439.

R. Re et al, Antioxidant activity applying an improved ABTS radical cation decolorization assay, Free Radical Biological Medicine, 1999, 26: 1231-1237.

F.W.P.C. van Overlveld et al, Tyrosine as important contributor to the antioxidant capacity of seminal plasma, Chemical and Biological Interactions, 2000, 127: 151-161.

Valhmu, W.B. et al, Structure of the human aggrecan gene: exon-intron organization and association with the protein domains, Biochem. J. 1995. vol. 309, pp. 535-542.

Pelligrini, A. et al, Proteolytic fragments of ovalbumin display antimicrobial activity, Biochimica Et Biophysica Acta. 2004. vol. 1672, pp. 76-85.

Hideo, H., Antioxidative activity of ovalbumin hydrolysates and their synergistic effects with alpha-tocopherol, Journal of the Japanese Society for Food Science and Technology, 1996, vol. 43, pp. 719-722.

\* cited by examiner

BIOACTIVE PEPTIDES DERIVED FROM THE PROTEINS OF EGG WHITE BY MEANS OF ENZYMATIC HYDROLYSIS

RELATED APPLICATIONS

The present application is a Continuation of co-pending PCT Application No. PCT/ES2004/070059, filed Jul. 23, 2004 which in turn, claims priority from Spanish Application Serial No. P200301829, filed on Jul. 31, 2003. Applicants claim the benefits of 35 U.S.C. §120 as to the PCT application and priority under 35 U.S.C. §119 as to said Spanish application, and the entire disclosures of both applications are incorporated herein by reference in their entireties.

SECTOR OF THE ART

The invention consists of the production of bioactive ovoproducts derived from the proteins of egg white. Following an enzymatic treatment, these give rise to peptides with inhibiting activity of the angiotensin converting enzyme (ACE inhibiting activity) in vitro and/or anti-hypertensive activity and/or antioxidant activity, which can be applied in the food and pharmaceutical industries.

STATE OF THE ART

The role of egg in human nutrition is essential since it constitutes a nourishing and healthy food source. The recent development of new biotechnological and separation techniques permits the fractionating of different egg components in order to be used with new food or non-food purposes, and thus new applications are appearing which contribute to increase their consumption. So, different companies concerned with the production of isolated proteins isolated from egg fractions are interested in increasing and diversifying the use of some components, such as ovalbumin and ovotransferin. This is the case with industries concerned with the production of lysozyme, used as an anti-microbial agent, which obtain other low cost nitrogenated fractions as byproducts, generally destined for animal food or for use as emulsifiers and gelling agents in different foods.

In recent years, functional foods have strongly irrupted in the food sector owing to the greater awareness of consumers to the relation existing between diet and health. Within functional ingredients, i.e., components which, incorporated into the food, provide it with specific biological activities that go beyond mere nutrition, bioactive peptides occupy an outstanding place on account of their diversity and multi-functionality. Bioactive peptides correspond to fragments that are inactive inside the precursor protein but which can be released by means of hydrolysis in vivo or in vitro, and in this way exert different physiological functions in the organism. Since their discovery in 1979, peptides have been described derived from food proteins with different biological activities: anti-hypertensive, anti-thrombotic, opiacious, antioxidant, immuno-modulating, etc.

Standing out among bioactive peptides are those which exert anti-hypertensive activity by means of regulating the renin-angiotensin system (T. Takano, Milk derived peptides and hypertension reduction, International Dairy Journal, 1998, 8: 375-381). The high incidence of coronary illnesses in the population is well known, and treatment of hypertension constitutes one of the strategies most used for reducing the risk of cardiovascular illnesses. The action mechanism of these peptides has been explained by means of inhibition of the angiotensin converting enzyme (ACE), which catalyses the formation of angiotensin II, an octapeptide with a potent vasoconstricting activity and which, moreover, deactivates bradykinin, which produces vasodilation. Different peptides have been discovered with ACE inhibiting (ACEI) activity obtained from enzymatic hydrolysates of whey proteins (WO01/85984, Enzymatic treatment of whey proteins for the production of antihypertensive peptides, the resulting products and treatment of hypertension in mammals), caseins (U.S. Pat. No. 6,514,941, Method of preparing a casein hydrolysate enriched in anti-hypertensive peptides), etc.

Another group of bioactive peptides of great importance is that of peptides with antioxidant activity. Ageing and various pathologies (neurological disturbances, cancers, cataracts, etc.) are related to oxidation of cell components such as lipids, proteins or DNA, so the inclusion of antioxidants in the diet has a preventive nature. In addition to their antioxidant activity, these compounds can prevent the oxidation of fats, thus avoiding the appearance of disagreeable odours in food. Some researches have demonstrated the capacity of different proteins and hydrolysates of them to exert an antioxidant action, either acting as scavengers of free radicals (K. Suetsuna, H. Ukeda and H. Ochi, Isolation and characterization of free radical scavenging activities peptides derived from casein, Journal of Nutritional Biochemistry, 2000, 11: 128-131) or inhibiting enzymes related to the oxidation of fats (S. G. Rival, S. Fornaroli, C. G. Boeriu and H. J. Wichers, Caseins and casein hydrolysates. I. Lipoxygensase inhibitory properties, Journal of Agricultural and Food Chemistry, 2001, 49: 287-294). It has to be highlighted that studies of the structure-activity, relation of ACEI peptides and antioxidants have revealed a characteristic common to both: the importance of certain hydrophobic amino acids in these two biological activities (H. M. Chen, K. Muramoto, F. Yamauchi, K. Fujimoto and K. Nokihara. Antioxidative properties of histidine-containing peptides designed from peptide fragments found in the digests of soybean protein, Journal of Agricultural and Food Chemistry, 1998, 46: 49-53).

Standing out among the strategies most used for obtaining active peptides for food use, are enzymatic hydrolysis and fermentation processes. Moreover, in the last few years different technological treatments have been put forward for the functionalisation of proteins. The use of high hydrostatic pressures as a physical method of denaturalisation has the result of modifying non-covalent bonds responsible for the structure of the proteins, giving rise to conformational changes leading to an unfolded state. Various studies have demonstrated that proteolysis is accelerated and different hydrolysis products appear under high pressure conditions, in comparison with what occurs at atmospheric pressure (F. Bonomi, A. Fiocchi, H. Frøkiaer, A. Gaiaschi, S. Iametti, C. Poesi, P. Rasmussen, P. Restani and P. Rovere, Reduction of immunoreactivity of bovine β-lactoglobulin upon combined physical and proteolytic treatment, Journal of Dairy Research, 2003, 70: 51-59). It must also be borne in mind that the majority of enzymes maintain their activity up to 400 MPa, becoming inactive at higher pressures. Nevertheless, the production of bioactive peptides under high pressure conditions has not been described in the literature.

Unlike other food proteins, there exist very few studies related to bioactive peptides derived from egg proteins, even though egg is a very important source of nitrogen in the diet. H. Fujita, K,. Yokoyama and M. Yoshikawa (Classification and antihypertensive activity of angiotensin I-converting enzyme inhibitory peptides derived from food proteins, Journal of Food Science, 2000, 65: 564-569) found ACEI activities in ovalbumin hydrolysates with pepsin and thermolysin with values of $IC_{50}$ (concentration which inhibits 50% of the enzyme's activity) of 45.0 and 83.0 µg/ml respectively. These authors isolated six peptides with ACEI activity starting from the hydrolysate with pepsin, with $IC_{50}$ values from 0.4 to 15 µM, though none of them, apart from the dipeptide LW, displayed anti-hypertensive activity in spontaneously hypertensive rats (SHR). It was postulated that such peptides would be substrates of ACE but not real inhibitors, and so would display apparent ACEI activities in the in vitro assay (H. Fujita and M. Yoshikawa, LKPNM: a prodrug-type ACE-inhibitory peptide derived from fish protein, Immunopharmacology, 1999, 44: 123-127). These observations demonstrate that, although it is a good starting point for work, in vitro ACEI activity cannot be the sole criterion for selection, since it does not take into consideration the physiological transformations in the organism determining the bioavailability of the peptides (digestion and passage through the gastrointestinal barrier in order to reach the blood in an active form).

Two peptides with vasodilatory activity have been described, coming from the same region of ovalbumin hydrolysed with different enzymes. H. Fujita, H. Usui, K. Kurahashi and M. Yoshikawa (Isolation and characterization of ovokinin, a bradykinin B1 agonist peptide derived from ovalbumin, Peptides, 1995, 16: 785-790) found that ovokinin, an octapeptide isolated from an ovalbumin hydrolysed with pepsin (FRADHPFL) (SEQ. ID. NO: 5), displayed vasorelaxing activity in canine mesenteric arteries, but they did not possess ACEI activity. Ovokinin possessed anti-hypertensive activity when administered orally to spontaneously hypertensive rats (SHR) at doses of 100 mg/kg (H. Fujita, R. Sasaki, and M. Yoshikawa, Potentiation of the antihypertensive activity of orally administered ovokinin, a vasorelaxing peptide derived from albumin, by emulsification in egg phosphatidylcholine, Bioscience Biotechnology and Biochemistry, 1995, 59; 2344-2345). N. Matoba, H. Usui, H. Fujita and M. Yoshikawa (A novel anti-hypertensive peptide derived from ovalbumin induces nitric oxide-mediated vasorelaxation in an isolated SHR mesenteric artery, FEBS Letters, 1999, 452: 181-184), starting from a hydrolysate of ovalbumin with chymotrypsin, purified a hexapeptide corresponding to a 2-7 fragment of ovokinin (RADHPF (SEQ. ID. NO: 9), ovokinin (2-7)) which exerted a potent vasodilatory action in SHR at doses of 10 mg/kg.

Later on, analogues of ovokinin (2-7) were synthesised with the aim of increasing its anti-hypertensive activity. Among them, RPFHPF (SEQ. ID. NO: 10) and RPLKPW (SEQ. ID. NO: 11) respectively displayed 10 and 100 times more activity than ovokinin (2-7) following administration to SHRs (minimum effective doses of 1 and 0.1 mg/kg) which was attributed to a greater resistance of the digestive tract to proteases (N. Matoba, Y. Yamada, H. Usui, R. Nakagiri and M. Yoshikawa, Designing potent derivatives of ovokinin (2-7), an anti-hypertensive peptide derived from ovalbumin, Bioscience Biotechnology and Biochemistry, 2001, 65: 736-739 and Y. Yamada, N. Matoba, H. Usui and K. Onishi, Design of a highly potent anti-hypertensive peptide based on ovalbumin (2-7), Bioscience Biotechnology and Biochemistry, 2002, 66: 1213-1217). It has to be highlighted that, according to these authors and unlike the majority of anti-hypertensive peptides of food origin, neither ovokinin (2-7), nor its RPFHPF (SEQ. ID. NO: 10) or RPLKPW (SEQ. ID. NO: 11) derivatives possessed ACEI activity. It has been postulated that they would lower arterial pressure via their interaction with receptors of the gastrointestinal tract or due to effects in the central nervous system.

Given the high biological quality of egg proteins, it is of great interest to obtain bioactive peptides starting from them which, consumed as part of one's diet, would, as well as exerting their basic nutritional functions, also be capable of producing metabolic or physiological effects useful in maintaining health. The production of bioactive peptides from egg white proteins would permit new uses to be found for chicken eggs, beyond their classical food value, including the production of medicinal and nutraceutical bioproducts. This would help in the development of healthy, safe and high quality foods, contributing to the utilisation and reassessment of ovoproducts.

DESCRIPTION OF THE INVENTION

Brief Description of the Invention

The present invention consists of the production of ovoproducts containing bioactive peptides with ACEI activity in vitro and/or anti-hypertensive activity and/or antioxidant activity, by means of enzymatic hydrolysis of egg proteins.

The bioactive peptides are produced by means of hydrolysis of one or more proteins, peptides or fragments thereof, containing the amino acid sequence of those bioactive peptides (preferably containing ovalbumin), using enzymes (preferably pepsin) and hydrolysis conditions which permit the breakage of each protein chain in the right places for their release. They can also be obtained by means of chemical or enzymatic synthesis or by means of recombinant methods, etc. Said peptides can be consumed as such, or on the basis of raw hydrolysates, of low molecular weight concentrates or of other active subfractions obtained by means of size separation methods or chromatography methods.

As well as forming food products, such hydrolysates, their fractions or the peptides could also form part of pharmaceutical products. So, they could help in the treatment and prevention of illnesses, particularly in control of arterial pressure. The invention expands the applications of egg proteins, contributing to their exploitation and reassessment.

Detailed Description of the Invention

The invention provides a method for producing active peptides starting from egg white proteins. These bioactive peptides are identified with the amino acid sequences shown in SEQ. ID. No 1, SEQ. ID. No 2, SEQ. ID. No 3, SEQ. ID. No 4, SEQ. ID. No 5, SEQ. ID. No 6, SEQ. ID. No 7 and SEQ. ID. No 8 (table 1), some of which possess ACEI activity in vitro and/or anti-hypertensive activity in vivo and/or antioxidant activity.

The starting material for the present invention would be any appropriate substrate comprising one or more proteins or peptides, of animal or plant origin or coming from microorganisms, and which contain the amino acid sequence of the bioactive peptides of interest (SEQ. ID. No 1, SEQ. ID. No 2, SEQ. ID. No 3, SEQ. ID. No 4, SEQ. ID. No 5, SEQ. ID. No 6, SEQ. ID. No 7 and SEQ. ID. No 8, table 1), preferably ovalbumin or egg white. Given that they all belong to the ovalbumin sequence, it is obvious that any preparation containing ovalbumin or peptides or fragments of ovalbumin of any size could be used, whether on their own or mixed with other proteins. For example: pure ovalbumin, egg white and whole egg in its different presentation forms, ovoproducts intended for the catering and restaurant trade, dietary complements for sportsmen, ovoproducts for animal food, etc.

Said starting material is dissolved or dispersed, at a suitable concentration, in water or a buffer solution, at a suitable pH for the action of the proteolytic enzyme. Any proteolytic enzyme can be used capable of breaking the protein present in the starting material and providing the peptides of interest, though preferably pepsin at pH 2.0-3.0. Proteolytic microorganisms carrying out a fermentation of the substrate could also be used.

The hydrolysis conditions: pH, temperature, pressure, enzyme/substrate ratio, interruption of the reaction, etc., are optimised with the aim of selecting the most active hydrolysates. In a particular embodiment, bioactive peptides are obtained using pepsin at pH 2.0, in an enzyme/substrate ratio of 1/100, w/w and carrying out the hydrolysis at 37° C. at atmospheric pressure (0.1 MPa), for a period of time between 10 minutes and 24 hours, though preferably for a period of time less than 3 hours. The use of high hydrostatic pressure, up to 400 MPa, accelerates the hydrolysis of the substrate without inhibiting the proteolytic enzyme and modifies the profile of the peptides obtained.

Next, if it is wished to concentrate the bioactive peptides and given that peptides with ACEI activity contain approximately from 3 to 6-7 amino acids (A. Pihlanto-Lippälä, T. Rokka and H. Korhonen, Angiotensin-l-converting enzyme inhibitory peptides derived from bovine milk proteins, International dairy Journal, 1998, 8: 325-331), low molecular weight fractions can be obtained from the hydrolysates by means of methods such as ultrafiltration, dialysis, electrodialysis with membranes of the right pore size, gel filtration chromatography, etc. In a particular embodiment, fractions of the hydrolysates are obtained of molecular weight below 3000 Da by means of ultrafiltration through a hydrophilic membrane of 3000 Da. Said fractions display greater ACEI and anti-hypertensive activity than the starting hydrolysates. Starting from the low molecular weight fractions of the hydrolysates, active subfractions can be isolated by means of hydrophobic interaction chromatography, ion exchange chromatography or preferably reverse phase high performance chromatography.

In addition to the complete hydrolysates and their fractions, the peptides shown in table 1 and designated with the SEQ. ID. No 1, SEQ. ID. No 2, SEQ. ID. No 3, SEQ. ID. No 4, SEQ. ID. No 5, SEQ. ID. No 6, SEQ. ID. No 7 and SEQ. ID. No 8 possess bioactive properties, fundamentally ACEI and/or anti-hypertensive and/or antioxidant activity and are also the object of the present invention. Specifically, the peptides identified with the sequences SEQ. ID. No 2, SEQ. ID. No 3, SEQ. ID. No 5 and SEQ. ID. No 6 show a potent ACEI activity in vitro and sequences SEQ. ID. No 2, SEQ. ID. No 3 and SEQ. ID. No 6 possess anti-hypertensive activity in spontaneously hypertensive rats (SHR) but not in normotensed Wistar-Kyoto rats (WKY) when administered via the oral route. Moreover, at least the peptide identified as SEQ. ID. No 6 possesses antioxidant activity towards free radicals. It should be emphasised that these are natural peptides in which few side effects and good tolerance are to be expected.

Likewise, bioactive peptides identified in the hydrolysates (SEQ. ID. No 1, SEQ. ID. No 2, SEQ. ID. No 3, SEQ. ID. No 4, SEQ. ID. No 5, SEQ. ID. No 6, SEQ. ID. No 7 and SEQ. ID. No 8) can be obtained by chemical and/or enzymatic synthesis of peptides or by recombinant methods.

TABLE 1

| Sequences of identified bioactive peptides | |
|---|---|
| YQIGL | SEQ. ID. N° 1 |
| IVF | SEQ. ID. N° 2 |
| RADHPFL | SEQ. ID. N° 3 |
| FSL | SEQ. ID. N° 4 |
| FRADHPFL* | SEQ. ID. N° 5 |

TABLE 1-continued

| Sequences of identified bioactive peptides | |
|---|---|
| YAEERYPIL | SEQ. ID. N° 6 |
| RDILNQ | SEQ. ID. N° 7 |
| SALAM | SEQ. ID. N° 8 |

*Sequence previously identified as ovokinin (H. Fujita, H. Usui, K. Kurahashi and M. Yoshikawa, Isolation and characterization of ovokinin, a bradykinin B1 agonist peptide derived from ovalbumin, Peptides, 1995, 16:785-790). It ought to be emphasised that these authors checked its vasodilatory activity in canine mesenteric arteries but they claim that it does not possess ACEI activity.

The obtaining of bioactive peptides from hydrolysates of egg white with pepsin has not previously been described even though the in vitro ACEI activity of ovalbumin hydrolysates had already been demonstrated (H. Fujita, K. Yokoyama and M. Yoshikawa (Classification and antihypertensive activity of angiotensin I-converting enzyme inhibitory peptides derived from food proteins, Journal of Food Science, 2000, 65: 564-569). Egg white turns out to be a cheap and easily accessible protein substrate for producing bioactive peptides. Furthermore, nor had the in vivo anti-hypertensive activity of ovalbumin hydrolysates been demonstrated. As already explained, it ought to be emphasised that very often many peptides which show themselves to be potent inhibitors of ACE in vitro lose all or part of their activity when tested in vivo, or even peptides which in vitro do not display any great activity as ACE inhibitors acquire such activity in vivo owing to the action of digestive enzymes (M. Maeno, N. Yamamoto and T. Takano, Identification of an anti-hypertensive peptide from casein hydrolysate produced by a proteinase from *Lactobacillus helveticus* CP790, Journal of Dairy Science, 1996, 79: 1316-1321).

These ovoproducts: the complete hydrolysates, the low molecular weight fractions thereof, or one or more of their constituent bioactive peptides (including their derivatives, their acceptable pharmaceutical salts and their mixtures), could be used as therapeutic substances with ACEI activity and/or with anti-hypertensive activity and/or with antioxidant activity. Said ovoproducts can be subjected to a heat treatment, such as pasteurisation, or be subjected to drying, freeze-drying, etc., in order to be used as functional food products, food additives or ingredients, or pharmaceutical products, for the treatment and/or prevention of arterial hypertension in all its forms, mainly in human beings, through also in animals. The quantity of hydrolysate, low molecular weight fraction, peptides, their derivatives or pharmaceutically acceptable salts and their mixtures, along with their dosage for the treatment of any particular pathology, will vary depending on numerous factors, such as age, severity of the pathology or dysfunction, administration route and frequency of the dose. These compounds can be presented in any form of administration, solid or liquid, and can be administered by any appropriate route, oral, respiratory, rectal or topical, though they are particularly designed for solid or liquid administration by oral route.

In general, the process of obtaining these ovoproducts: the complete hydrolysates, the low molecular weight fractions thereof and their constituent peptides, will be able to be optimised by aiming for the production of the greatest possible amount of bioactive peptides or for controlling as far as possible the appearance of bitterness, normally caused by a high concentration of intermediate or low molecular weight hydrophobic peptides.

Analytical Procedures

Measurement of the Inhibitory Activity of the Angiotensin Converting Enzyme (ACEI Activity)

The inhibitory activity of the angiotensin converting enzyme (ACE) is measured in vitro according to the method of D. W. Cushman and H. S. Cheung (Spectrophotometric assay and properties of the angiotensin-converting enzyme of rabbit lung. Biochemical Pharmacology, 1971, 20: 1637-1648), later on modified by Y. K. Kim, S. Yoon, D. Y. Yu, B. Lönnerdal and B. H. Cheung (Novel angiotensin-I-converting enzyme inhibitory peptides derived from recombinant human $\alpha_{s1}$-casein expressed in *Escherichia coli*, Journal of Dairy Research 1999, 66, 431-439).

The substrate hippuryl histidyl leucine (HHL, Sigma Chemicals Co., St. Louis, Mo., USA) is dissolved in a 0.1 M borate buffer with 0.3 M NaCl pH 8.3 to obtain a final concentration of 5 mM. To 100 μl of substrate are added 40 μl of each of the samples whose ACEI activity it is wished to determine. The ACE enzyme (EC 3.4.15.1, Sigma) is added, dissolved in 50% glycerol and diluted 1/10 in bidistilled water at the moment of conducting the assay. The reaction is carried out at 37° C. for 30 minutes in a water-bath. The enzyme is deactivated by lowering the pH with 150 μl of 1 N HCl. The hippuric acid formed is extracted with 1000 μl of ethyl acetate. Following vortex stirring for 20 seconds, it is centrifuged at 4000 rpm for 10 minutes at room temperature. 750 μl of the organic phase are taken and evaporated by heating at 95° C. for 10 minutes. The hippuric acid residue is redissolved in 800 μl of bidistilled water and, following stirring for 20 seconds, the absorbency at 228 nm is measured in a Dur-70 spectrophotometer from Beckman Instruments, Inc., Fullerton, USA.

In order to calculate the percentage of ACEI activity, the following formula is used $$\% ACEI \frac{Acontrol - Asample}{Acontrol - Ablank} * 100$$

The blank is used for correcting the background absorbency. This contains substrate, enzyme and 20 μl of bidistilled water in place of the sample, and the reaction is halted at zero time. The control implies a hundred percent of the enzymatic action on the substrate in the absence of inhibitors and contains 20 μl of water in place of the sample and is incubated the same time as the sample.

The results are presented as the $IC_{50}$ (μM or μg/ml) or concentration at which 50% of the enzyme's activity is inhibited. The concentration of protein is determined by means of the bicinchonomic acid (BCA) assay (Pierce, Rockford, Ill., USA) using bovine seroalbumin as reference.

Measurement of the Antioxidant Activity

In order to measure the antioxidant activity, the method developed by R. Re, N. Pellegrini, A. Proteggente, A. Pannala, M. Yang and C. Rice-Evans (Antioxidant activity applying an improved ABTS radical cation decolorization assay, Free Radical Biological Medicine, 1999, 26: 1231-1237) is used. The method is based on the disappearance of the radical $ABTS^{\cdot +}$ (2,2-azinobis(3-ethylbenzothiazoline-6-sulphonic) acid) owing to the reducing action of different samples with antioxidant activity. The radical $ABTS^{\cdot +}$ displays a maximum absorbency at 734 nm. The antioxidant activity is detected by the fall in the 734 nm absorbency time.

In order to generate the radical $ABTS^{500 \cdot +}$, the compound ABTS (Sigma), dissolved in water at a concentration of 7 mM, is brought into contact with 2.45 mM potassium persulphate in a ratio of 1:2 for 24 hours in the absence of light. After 24 hours, the absorbency at 734 nm is adjusted to a value of 0.70 ±0.02 with 5 mM of phosphate buffer salt (PBS), 138 mM of NaCl, pH =7.4. In a standard experiment, 1 ml of this solution is added to 10 μl of the sample (1.5 mM) dissolved in 0.02 M sodium phosphate buffer, pH =6.5 The experiment is conducted in triplicate, with each sample being incubated with the radical $ABTS^{\cdot +}$ for 10 minutes at 37° C., with readings of the absorbency at 734 nm being taken at 1, 6 and 10 minutes. Used as blank is 0.02 M sodium phosphate buffer, pH =6.5 and at the same time as the incubation of the samples is carried out, the radical $ABTS^{500 \cdot +}$ is incubated without any antioxidant agent (control). The antioxidant activity of each sample is calculated with respect to the absorbency at 734 nm shown by the control. The antioxidant activity of the sample is expressed in relation to the antioxidant activity of TROLOX® (6-hydroxy-2,5,7,8-tetramethylchroman-2-carboxylic acid) (Sigma), analogous to vitamin E, by means of a TEAC value (Trolox equivalent antioxidant capacity) at a certain time.

Different ways of calculating the TEAC value have been developed. We use the method described by F. W. P. C. van Overlveld, G. R. M. M. Haenen, J. Rhemrev, J. P. W. Vermeiden and A. Bast (Tyrosine as important contributor to the antioxidant capacity of seminal plasma, Chemical and Biological Interactions, 2000, 127: 151-161), which is valid for calculating the TEAC value of a pure compound, which provokes a decrease in the absorbency which linearly increases as the concentration is increased. In this case, it would only be necessary to calculate a certain concentration of a compound in order to be able to calculate its TEAC value.

$$TEAC_{compound} \frac{\text{Variation in Abs}_{734\,nm}}{0.28045 \times [\text{Concentration of compound}]}$$

The value 0.2845 represents the decrease in absorbency caused by 1 mM of 6-hydroxy-2,5,7,8-tetramethylchroman-2-carboxylic acid.

Isolation of Peptide Fragments by Means of Reverse Phase High Performance Liquid Chromatography (RP-HPLC) at the Semi-Preparatory Scale Equipment is used consisting of two programmable pumps, Waters Delta 600 model, an aligned diodes detector model 966, an automatic injector model 717 plus, and an automatic fractions collector (Waters Corp, Mildford, Mass., USA). A $C_{18}$ Prep NovaPack® HR, 7.8×300 mm and pore size 6 gm (Waters) is used, with a $C_{18}$ (Waters) cartridge as column-guard. The analysis is conducted at 30° C. and the detection at 214 and 280 nm. The data gathering is done with Software Millennium version 3.2 (Waters). For the elution of the samples, a binary gradient is used consisting of water (phase A) and acetonitrile (phase B) with 0.1% TFA in each of them and a flow of 4 ml/min. The gradient of phase B is from 2% to 10% in 15 min, from 10% to 20% in 35 minutes, from 20% to 30% in 20 minutes, the column is washed with 70% of B and is finally conditioned under the starting conditions for 15 minutes. The volume of sample injected is 200 μl. Prior to the injection, the samples are passed through a membrane filter MILLIPORE® filter (Waters) of 0.45 μm.

Analysis by Means of Tandem Mass Spectrometry (Off-Line)

Esquire 3000 ion trap equipment is used (Bruker Daltonik GmbH, Bremen, Germany). The sample is injected in the electrospray sprayer at a flow of 4 μl/min, using a type 22 syringe pump (Harvard Apparatus, South Natick, Mass., USA). The equipment uses nitrogen as the sprayer and drying gas, and operates with a helium pressure of 5×10⁻³ bar. The mass spectra are acquired in an interval of 50-1500 m/z and at a speed of 13000 Da/second. The interpretation of the tandem MS spectra for identification of the peptide sequences is done with the Biotools 2.1 program (Bruker Daltonik GmbH, Bremen, Germany).

Analysis by Means of RP-HPLC Coupled On-Line to Tandem Mass Spectrometry (RP-HPLC-MS/MS)

Esquire-LC equipment is used (Bruker Daltonik GmbH, Bremen, Germany). The HPLC equipment (series 1100) consists of a quaternary pump, an automatic injector, a degasification system for eluents and a variable wavelength ultraviolet detector (Agilent Technologies, Waldbronn, Germany) coupled in line to an Esquire 3000 ion trap mass spectrometer (Bruker Daltonik). The column is a HI-PORE® C18 column (250×4.6 mm i.d. particle size 5 gm) (Bio-Rad Laboratories, Richmond, Calif., USA). Solvent A is a mixture of water and trifluoroacetic acid (1000:0.37) and solvent B is a mixture of acetonitrile and trifluoroacetic acid (1000:0.27). 50 µl of sample is injected at a concentration of 1-2 mg/ml. A flow of 0.8 ml/minute is used with a linear gradient of from 0% to 30% of solvent B in A in 25 minutes. The eluent is monitored at 214 mn by means of mass spectrophotometry under the same conditions as those stated in the previous section, apart from the fact that the injection of the sample via the sprayer is 60 µl/min.

Study of Antihypertensive Activity in Spontaneously Hypertensive Rats

The effect is studied of various identified peptides and of some products containing them (for example egg white hydrolysed with pepsin for 3 hours and the fraction of it less than 3000 Da) on the arterial pressure of spontaneously hypertensive rats (SHR) and Wistar-Kyoto rats (WKY) which are the normotense controls for the SHR.

This study is conducted with SHR (10) and WKY of 17-24 weeks old and weight between 300 and 350 g, coming from Charles River Laboratories España, S. A. The rats are kept in cages of five by five and maintained at a stable temperature of 25° C. with light-dark cycles of 12 hours, ingesting freely available water and food. In order to carry out the measurement of systolic arterial pressure (SAP) "tail cuff" equipment is used (Le5001, Letica) which automatically provides a digital value of the SAP and records and facilitates the cardiac frequency of the animals. Various measurements are made and the average of all of them is obtained in order to achieve a reliable value of the SAP. Before positioning the cuff and transducer in the tail of the rats, the rats are exposed to a temperature of close to 30° C. in order to facilitate dilation of the caudal artery. Also, in order to ensure the reliability of the measurement, the animals are made to get used to the procedure for two weeks prior to conducting each assay in question.

The administration of the products to be assayed is done by means of an intragastric probe in a time margin of between 9 and 10 o'clock in the morning. The SHR used for the study had SAP values of between 230 and 280 mm Hg. The WKY used for the study at that moment had SAP values of between 160 and 200 mm Hg. Measurements of the SAP were taken from the animals periodically, every 2 hours, up to 8 hours post-administration of the products to be assayed; in addition, a SAP measurement was taken 24 hours after the administration of those products. As negative control (in order to establish the circadian variation of the SAP in probed rats) the measurements of the SAP obtained in rats which had been administered 1 ml of water by means of intragastric probe were used. As positive control, the measurements of the SAP obtained in rats which had been administered 50 mg/kg of Captopril (prototype ACEI drug) by means of intragastric probe were used. This dose of Captopril was administered to each rat in a volume of 1 ml. In order to establish the effect of the unhydrolysed egg white on the arterial pressure of the animals, similar assays to those described above were conducted, in which the animals were treated by the same procedure with 200 mg/kg of previously freeze-dried egg white (reference).

The results obtained are grouped and the mean±the standard error of measurement (SEM) is obtained for a minimum of 9 homogenous assays. The data of the treated animals are always compared with the data deemed to be a negative control. In order to compare them and obtain the statistical significance, Student's t-test for unpaired data is used and the difference for values of $p<0.05$ is considered significant.

BRIEF DESCRIPTION OF THE CONTENT OF THE FIGURES

FIG. 1 represents the drop in systolic arterial pressure (SAP) obtained in spontaneously hypertensive rats following administration by means of intragastric probe of 1 ml of water (○), 50 mg/kg of Captopril (□), 200 mg/kg of egg white (EW) (×) and different doses of egg white hydrolysate (EWH): 100 mg/kg (◆), 150 mg/kg (▲), 200 mg/kg (■) and 400 mg/kg (Δ). The data represent the mean±SEM for a minimum of 9 animals. The abscissa represents time, in hours, passed since the administration.

FIG. 2 represents the drop in systolic arterial pressure (SAP) obtained in spontaneously hypertensive rats following administration by means of intragastric probe of 1 ml of water (○), 50 mg/kg of Captopril (□) and different doses of the fraction less than 3000 Da of egg white hydrolysate (F<3000 Da): 25 mg/kg (◆), 50 mg/kg (▲) and 100 mg/kg (■). The data represent the mean±SEM for a minimum of 9 animals. The abscissa represents time, in hours, passed since the administration.

Figure 4:
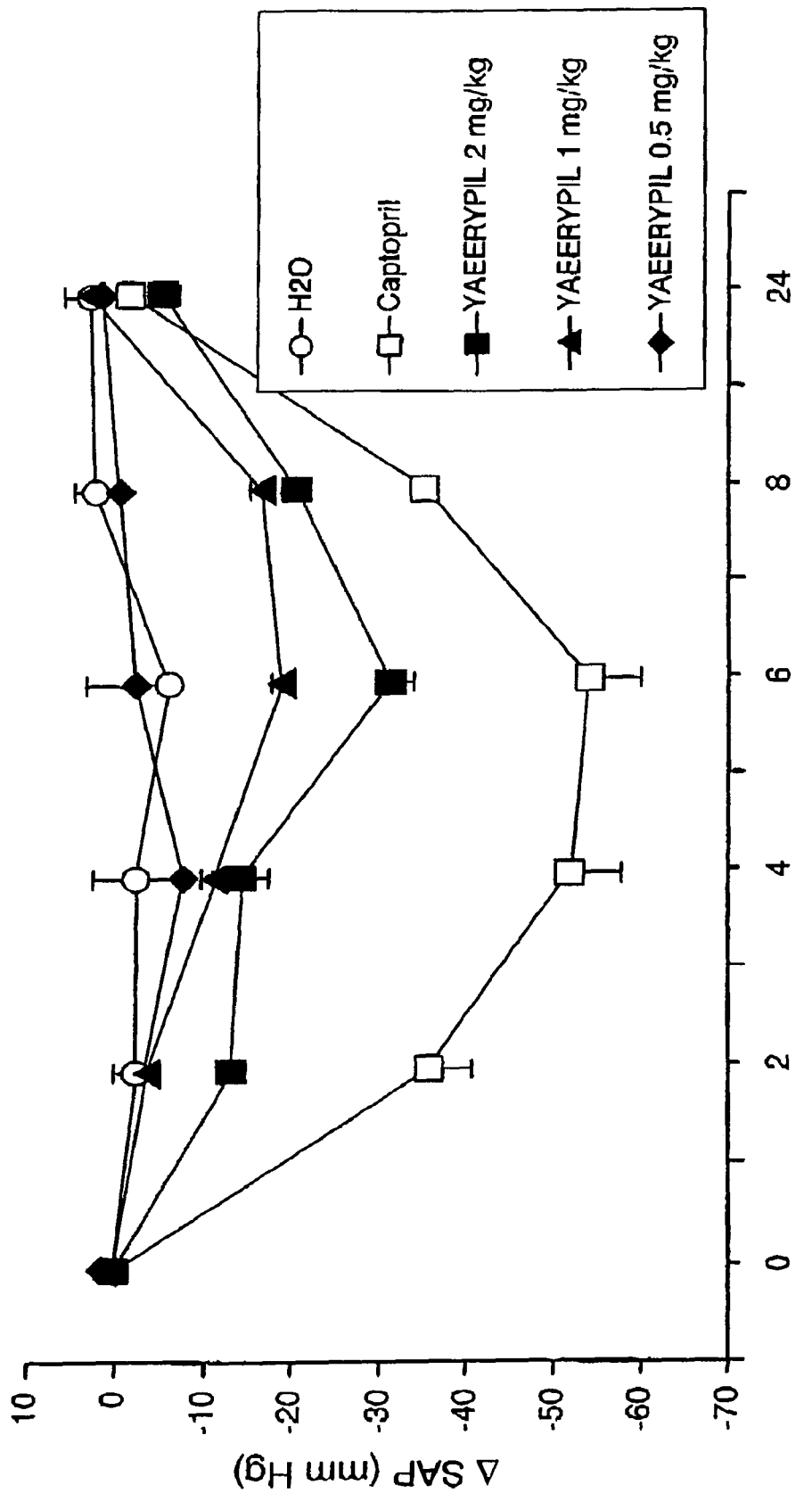

FIG. 4 represents the drop in systolic arterial pressure (SAP) obtained in spontaneously hypertensive rats following administration by means of intragastric probe of 1 ml of water (○), 50 mg/kg of Captopril (□) and different doses of the peptide YAEERYPIL (SEO. ID. NO: 6): 0.5 mg/kg (◆), 1 mg/kg (▲) and 2 mg/kg (■). The data represent the mean ± SEM for a minimum of 9 animals. The abscissa represents time, in hours, passed since the administration.

Figure 5:
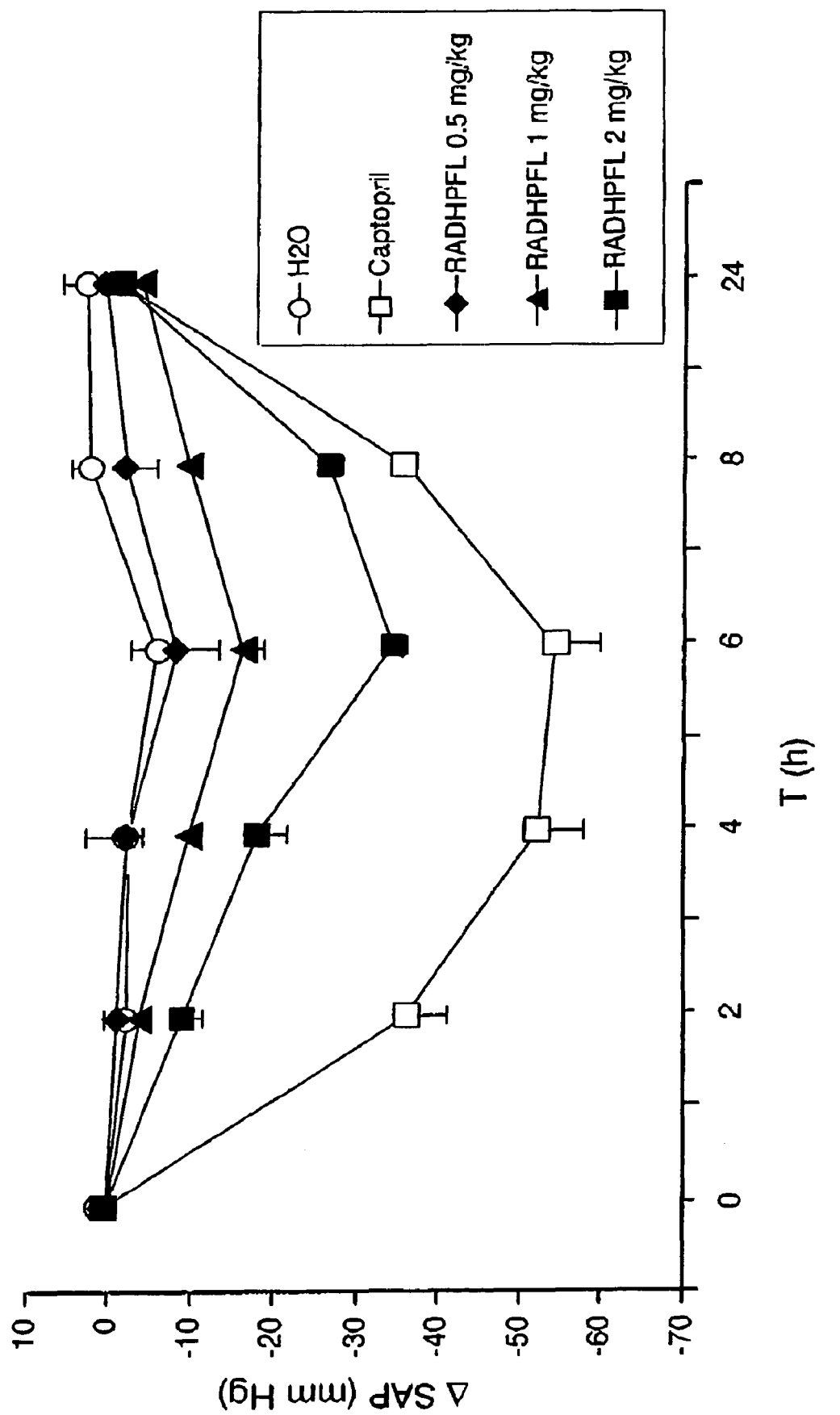

FIG. 5 represents the drop in systolic arterial pressure (SAP) obtained in spontaneously hypertensive rats following administration by means of intragastric probe of 1 ml of water (○), 50 mg/kg of Captopril (□) and different doses of the peptide RADHPFL (SEQ. ID. NO: 3): 0.5 mg/kg (◆), 1 mg/kg (▲) and 2 mg/kg (■). The data represent the mean±SEM for a minimum of 9 animals. The abscissa represents time, in hours, passed since the administration.

Figure 6:
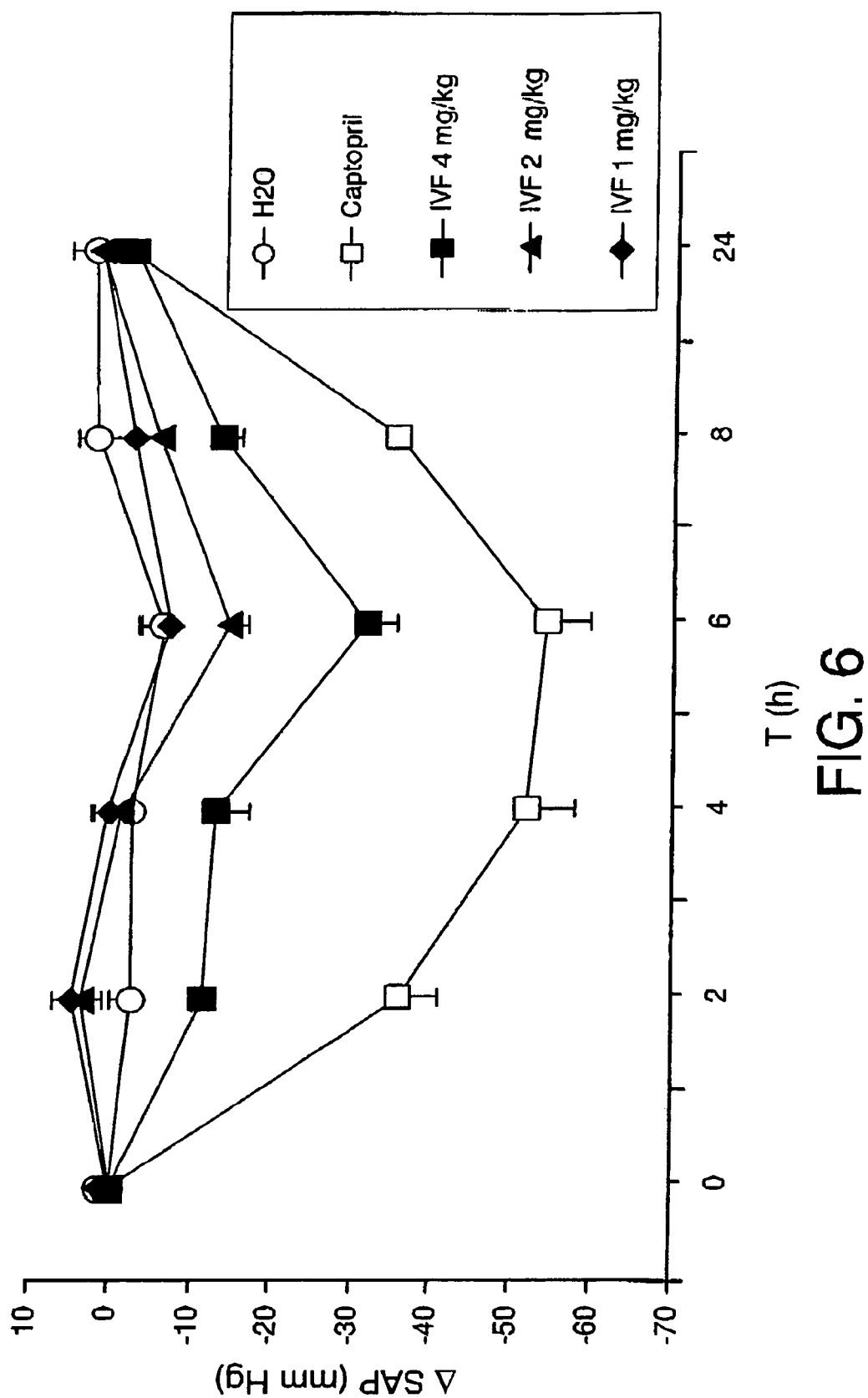

FIG. 6 represents the drop in systolic arterial pressure (SAP) obtained in spontaneously hypertensive rats following administration by means of intragastric probe of 1 ml of water (×), 50 mg/kg of Captopril (□) and different doses of the peptide IVF: 1 mg/kg (♦), 2 mg/kg (▲) and 4 mg/kg (■). The data represent the mean±SEM for a minimum of 9 animals. The abscissa represents time, in hours, passed since the administration.

Figure 7:
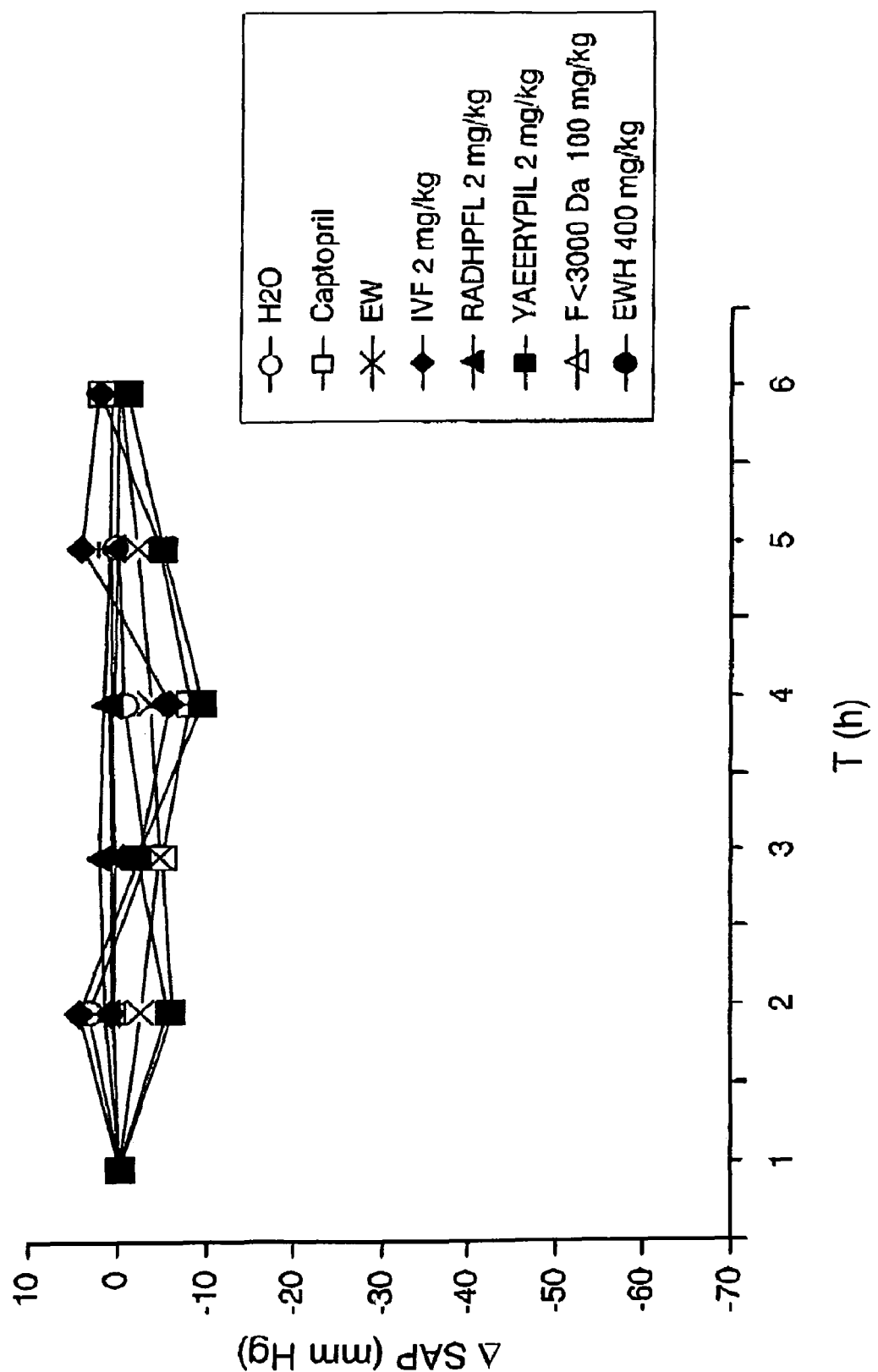

FIG. 7 represents the drop in systolic arterial pressure (SAP) obtained in Wistar—Kyoto normotense rats following administration by means of intragastric probe of 1 ml of water (○), 50 mg/kg of Captopril (□), 200 mg/kg of EW (×), 400 mg of EWH (•) 100 mg/kg of the fraction less than 3000 Da of EWH (F<3000 Da) (Δ), 2 mg/kg of the peptide YAEERYPIL (SEQ. ID. NO: 6) (♦), 2 mg/kg of the peptide RADHPFL (SEQ. ID. NO: 3) (▲) and 4 mg/kg of the peptide IVF (■). The data represent the mean±SEM for a minimum of 9 animals. The abscissa represents time, in hours, passed since the administration.

EXAMPLES OF EMBODIMENT OF THE INVENTION

The following examples illustrate the invention, though they must not be regarded as limiting the scope thereof.

Example 1

Obtaining of Bioactive Peptides, with ACEI and Anti-Hypertensive Activity, Starting from Egg White Hydrolysed with Pepsin at Atmospheric Pressure The hydrolysate was obtained using as substrate chicken egg white coming from fresh eggs, separated from the yolk and freeze-dried. As enzyme, pepsin was used (E.C. 3.4.23.1 type A, 10000 U/mg of protein) coming from pig stomach (Sigma). The substrate was dissolved in water at a concentration of 100 mg/ml and the pH was adjusted to 2.0 adding 1N HCl. Pepsin was added (enzyme/substrate ratio 1/100, w/w). The hydrolysis was conducted at a temperature of 37° C. for 24 hours, at atmospheric pressure (0.1 MPa). The deactivation of the pepsin was achieved by raising the pH to 7.0 with 1N NaOH.

The ACEI activity was measured in aliquots collected following different hydrolysis times, 0, 30 minutes, 3, 5, 8 and 24 hours. The results showed that unhydrolysed egg white did not possess ACEI activity ($IC_{50}$>750 μg/ml) but it actively inhibits ACE following different hydrolysis times with pepsin, reaching major inhibition after 3 hours of hydrolysis ($IC_{50}$=200.9±1.5 μg/ml, 55.3±2.1 μg/ml, 72.2±2.3 μg/ml, 43.07±1.4 μg/ml, 40.2±0.9 μg/ml, at 30 min, 3, 5 8 and 24 hours, respectively).

The fraction less than 3000 Da of egg white hydrolysed with pepsin for 3 hours was obtained by means of ultrafiltration via a hydrophilic membrane of 3000 Da (Centriprep, Amicon, Inc., Beverly, Mass., USA), centrifuging at 1900 g for 40 minutes. ACEI activity was measured in the retentate (fraction of size>3000 Da) and in the permeate (fraction of size<3000 Da). The values of $IC_{50}$ were respectively 298.4 and 34.5 μg/ml. This demonstrates that the permeate possesses approximately 10 times more ACEI activity and therefore the activity is fundamentally due to small size peptides.

The anti-hypertensive activity of egg white hydrolysed with pepsin for 3 hours and its fraction less than 3000 Da was assayed in spontaneously hypertensive rats (SHR) and in normotense Wistar-Kyoto rats (WKY). Different concentrations of both freeze-dried ovoproducts were administered to the animals which, in the case of the hydrolysate, were between 100 and 400 mg/kg, and in the case of the fraction less than 3000 Da between 25 and 100 mg/kg.

Figure 1:
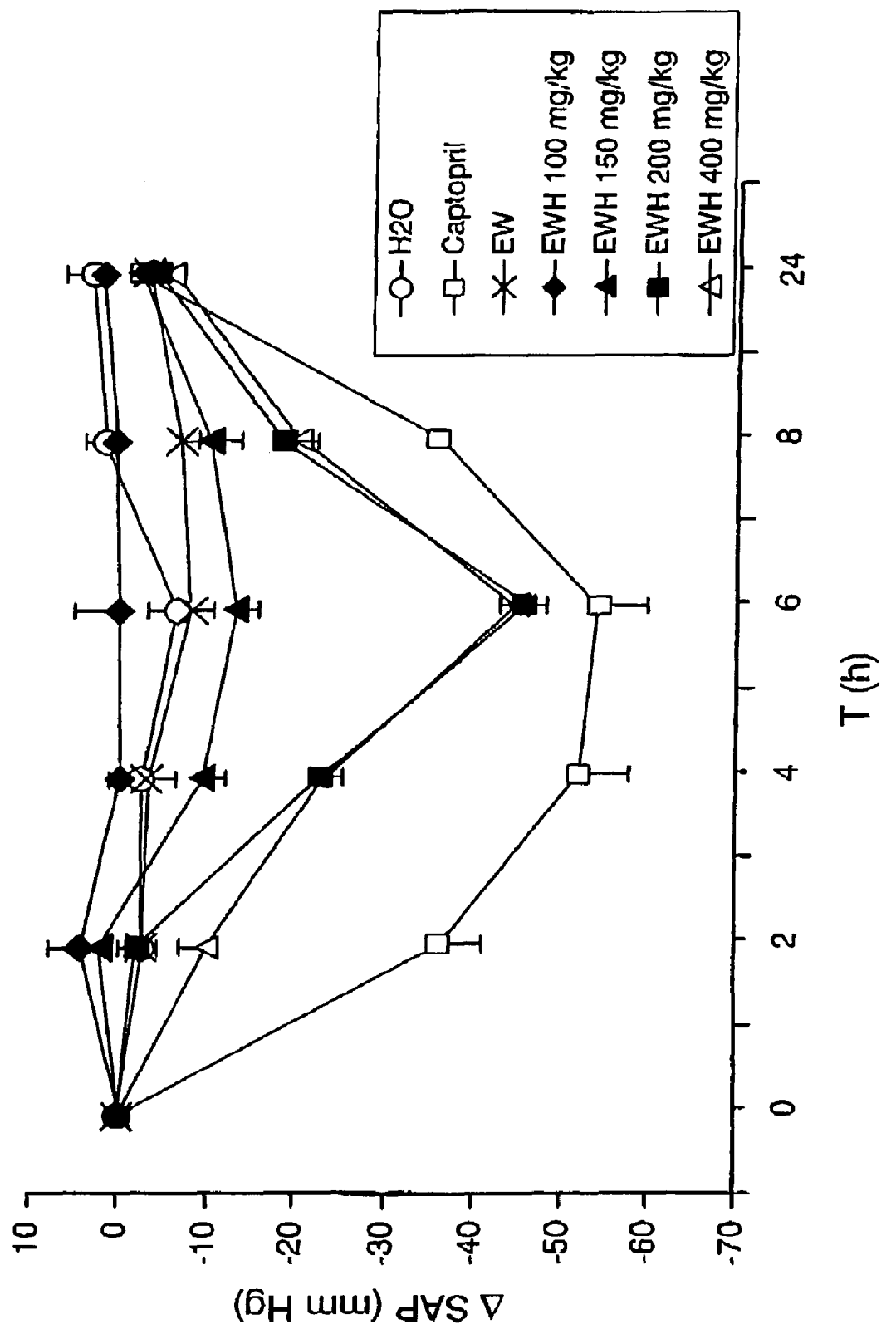
Figure 2:
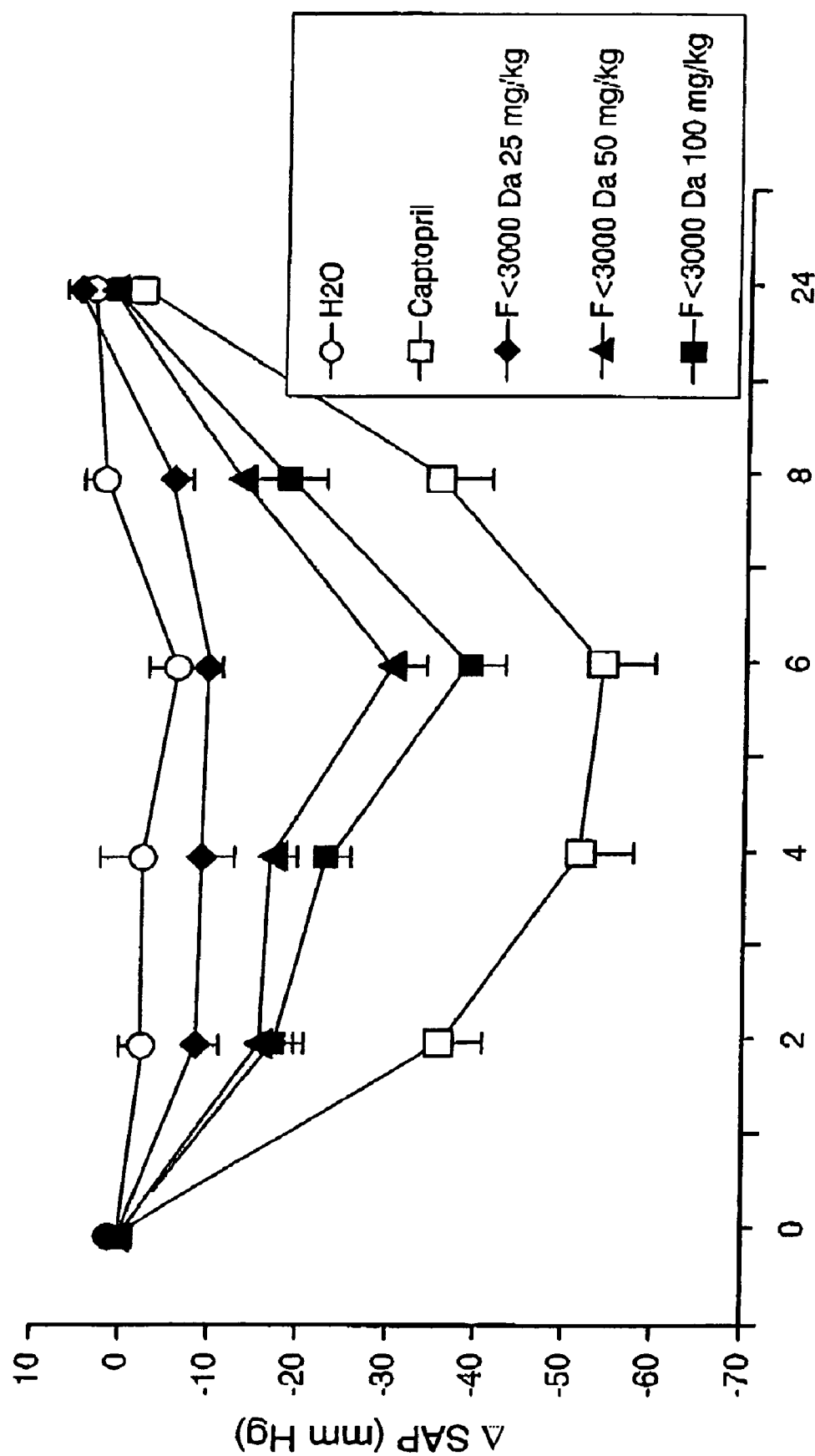

FIGS. 1 and 2 respectively show the drop in SAP obtained in SHR at different moments following the administration of different doses of egg white hydrolysed with pepsin for 3 hours, and following the administration of different does of the fraction less than 3000 Da of that hydrolysate. The results of these assays with unhydrolysed egg white (reference) (200 mg/kg) are represented in FIG. 1. In it, it can be seen that the SAP values corresponding to the reference are similar to the SAP values of animals which have been administered water. These figures also include the drop in SAP observed following the administration of Captopril. The Captopril produces a pronounced drop in SAP in the SHR. The drop in SAP is a maximum 6 hours after the administration of the drug. The egg white hydrolysate and the fraction less than 3000 Da occasion significant dose-dependent decreases in the SAP in the animals. The lower values of SAP following the administering of egg white hydrolysate and the fraction less than 3000 Da of this hydrolysate is also observed 6 hours after their administration. The values of SAP observed 24 hours after the different administrations are similar to those which the animals had before them.

Figure 3A:
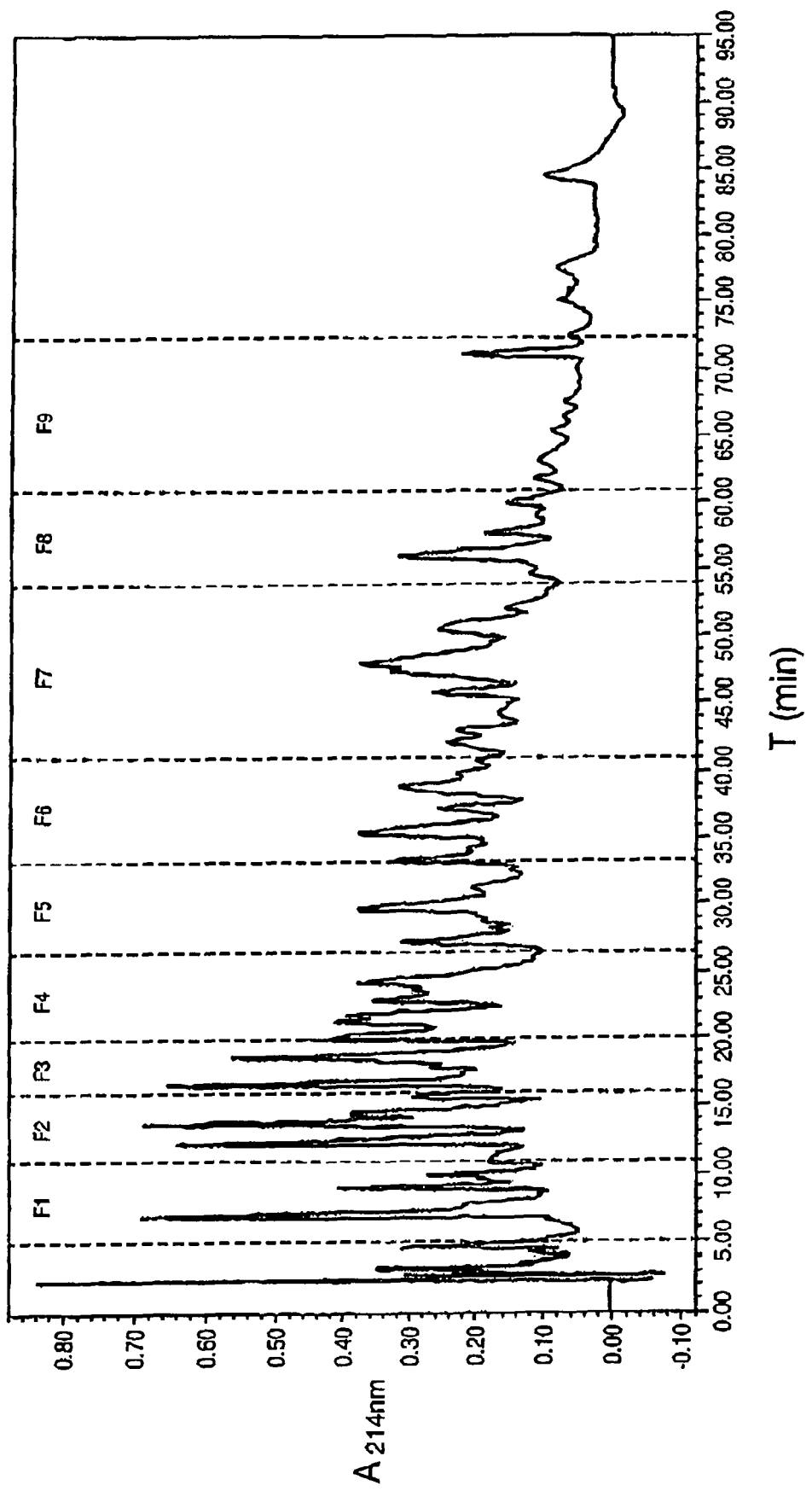
FIG. 3A is a chromatogram obtained using reverse phase high performance liquid chromatography (RP-HPLC) at the preparatory scale for the fraction less than 3000 Da produced by means of hydrolysis of egg white with pepsin for 3 hours, in which 9 fractions (F1-F9) are selected, which were collected automatically. The abscissa represents time in minutes.

With the aim of identifying the peptides responsible for ACEI and/or anti-hypertensive activity, the fraction less than 3000 Da obtained following hydrolysis of the egg white with pepsin for 3 hours was freeze-dried and redissolved in water at a concentration of 50 mg/ml and fractionated by means of RP-HPLC at the semi-preparatory scale. As shown in FIG. 3A, 9 fractions were collected (after approximately 10-12 analyses), which were frozen, freeze-dried and kept at −20° C. until use. Each fraction was dissolved in milli-Q water and the ACEI activity was measured.

Figure 3B:
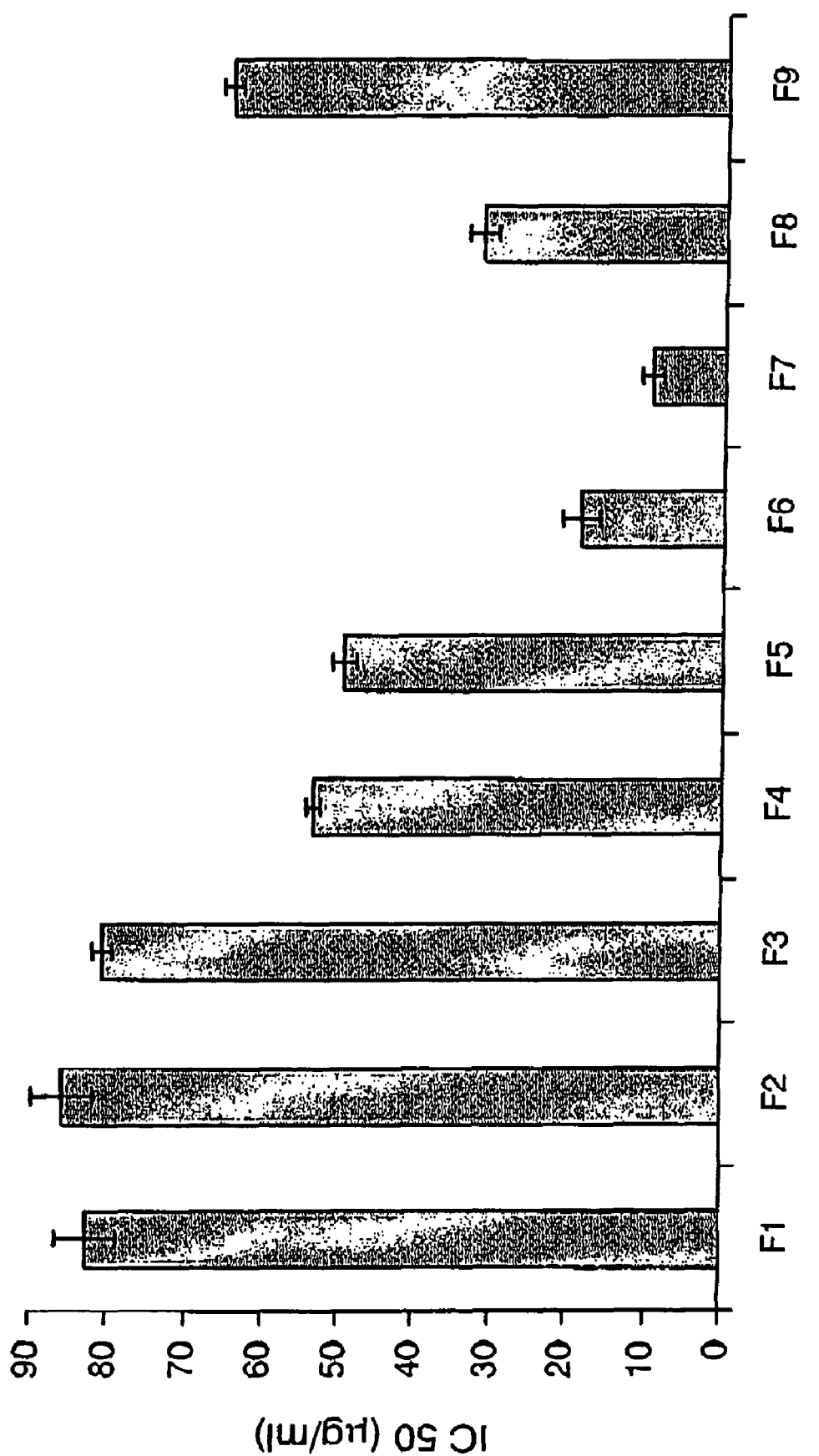
FIG. 3B represents the ACEI activity, expressed as the protein concentration needed for inhibiting 50% of the enzyme ($IC_{50}$), corresponding to each of the 9 fractions collected by means of the RP-HPLC at the preparatory scale.

As shown in FIG. 3B, the most active subfractions were 6, 7 and 8, which were analysed by tandem mass spectrometry in order to determine their constituent peptides. With that aim, the peptide subfractions 6, 7 and 8, collected by means of preparatory RP-HPLC, were freeze-dried and dissolved at a concentration of 5-10 μg/ml in a mixture of 50% acetonitrile in water containing 0.3% formic acid. The identified peptides are shown in table 2. It must be emphasised that all the peptides came from ovalbumin.

TABLE 2

Peptides identified in subfractions 6, 7 and 8 of the fraction less than 3000 Da of egg white hydrolysed with pepsin for 3 hours

| Fraction N°. | Experimental mass | Theoretical mass | Protein | Position | Amino acids Sequence | N° |
|---|---|---|---|---|---|---|
| 6 | 592.3 | 592.32 | Ovalbumin | 212-216 | YQIGL | SEQ. ID. N° 1 |
| 6 | 377.2 | 377.23 | Ovalbumin | 178-180 | IVF | SEQ. ID. N° 2 |
| 6 | 854.4 | 854.44 | Ovalbumin | 359-365 | RADHPFL | SEQ. ID. N° 3 |

TABLE 2-continued

Peptides identified in subfractions 6, 7 and 8 of the fraction less than 3000 Da of egg white hydrolysed with pepsin for 3 hours

| Fraction N°. | Experimental mass | Theoretical mass | Protein | Position | Amino acids | Sequence N° |
|---|---|---|---|---|---|---|
| 6 | 365.2 | 365.20 | Ovalbumin | 99-101 | FSL | SEQ. ID. N° 4 |
| 7 | 721.3 | 721.37 | Ovalbumin | 256-261 | ESIINF | SEQ. ID. N° 12 |
| 7 | 1001.4 | 1001.51 | Ovalbumin | 358-365 | FRADHPFL | SEQ. ID. N° 5 |
| 7 | 1152.3 | 1152.58 | Ovalbumin | 106-114 | YAEERYPIL | SEQ. ID. N° 6 |
| 8 | 757.2 | 757.41 | Ovalbumin | 84-89 | RDILNQ | SEQ. ID. N° 7 |
| 8 | 1040.2 | 1040.58 | Ovalbumin | 243-252 | VLLPDEVSGL | SEQ. ID. N° 13 |
| 8 | 491.1 | 491.24 | Ovalbumin | 36-40 | SALAM | SEQ. ID. N° 8 |
| 8 | 487.1 | 487.26 | Ovalbumin | 144-147 | ELIN | SEQ. ID. N° 14 |
| 8 | 1164.2 | 1164.59 | Ovalbumin | 125-134 | YRGGLEPINF | SEQ. ID. N° 15 |

Example 2

Peptides Obtained by Means of Chemical Synthesis with ACEI and Anti-Hypertensive Activity All the identified peptides mentioned in Table 2 of example 1 were chemically synthesised by means of the Fmoc method in solid phase with a model 431A synthesiser from Applied Biosystems Inc. (Überlingen, Germany). The purity of the synthetic peptides was verified by mean of RP-HPLC-MS/MS.

The ACEI activity of the synthetic peptides was measured. The activity found is shown in table 3. Standing out for their activity are 8 peptides with $IC_{50}$ less than 450 µM and above all the sequences: SEQ. ID. No 2, SEQ. ID. No 3, SEQ. ID. No 5 and SEQ. ID. No 6 with $IC_{50}$ less than 34 µM.

TABLE 3

ACEI activity of peptides identified in subfractions 6, 7 and 8 of the fraction less than 3000 Da of egg white hydrolysed with pepsin for three hours

| Sequence N° | Amino acids | $IC_{50}$ (µM) |
|---|---|---|
| SEQ. ID. N° 1 | YQIGL | 173.8 |
| SEQ. ID. N° 2 | IVF | 33.9 |
| SEQ. ID. N° 3 | RADHPFL | 6.2 |
| SEQ. ID. N° 4 | FSL | 172.9 |
| SEQ. ID. N° 12 | ESIINF | >1000 |
| SEQ. ID. N° 5 | FRADHPFL | 3.2 |
| SEQ. ID. N° 6 | YAEERYPIL | 4.7 |
| SEQ. ID. N° 7 | RDILNQ | 435.7 |
| SEQ. ID. N° 13 | VLLPDEVSGL | >1000 |
| SEQ. ID. N° 8 | SALAM | 229.1 |
| SEQ. ID. N° 14 | ELIN | >1000 |
| SEQ. ID. N° 15 | YRGGLEPINF | >1000 |

The anti-hypertensive activity of peptides SEQ. ID. No 2, SEQ. ID. No 3 and SEQ. ID. No 6 were assayed for which different doses of them were administered to SHR and WKY, the maximum dose used at all times being equivalent in units of ACEI activity to the dose 50 mg/kg of the fraction less than 3000 Da of the egg white hydrolysate. The peptides were dissolved in distilled water and the corresponding dose was administered to each rat in a volume of 1 ml.

FIGS. 4, 5 and 6 show the drops in SAP obtained in SHR at different moments, following administration of different doses of the peptides SEQ. ID. No 6, SEQ. ID. No 3 and SEQ. ID. No 2. It can be seen that the administration of these peptides occasions a significant dose-dependent drop in the SAP in these animals. The drop in SAP is maximum 6 hours after the administration of these peptides and the maximum drop obtained is also similar for the different peptides.

FIG. 7 shows the changes in the SAP obtained in WKY rats at different moments, following the administration of the following compounds: 400 mg/kg of egg white hydrolysate, 100 mg/kg of the fraction less than 3000 Da of the hydrolysate, 2 mg/kg of peptide SEQ. ID. No 6, 2 mg/kg of peptide SEQ. ID. No 3 and 4 mg/kg of peptide SEQ. ID. No 2. Also included are the results obtained following the administration of 50 mg/kg of Captopril. It can be seen that none of these compounds modifies the SAP of WKY rats when the highest dose used is administered. These results mean that possible undesirable effects of the assayed products on the arterial pressure of normotense subjects can be discarded.

The results presented show that the peptides identified by the sequences SEQ. ID. No 2, SEQ. ID. No 3 and SEQ. ID. No 6 have a clear and pronounced anti-hypertensive effect which, after their acute administration, follows a time course that is similar to the anti-hypertensive effect seen when egg white hydrolysate or the fraction less than 3000 Da of that hydrolysate are administered.

Example 3

Peptides Obtained by Means of Chemical Synthesis with Antioxidant Activity

The antioxidant activity of one of the identified peptides was measured, specifically, the sequence: SEQ. ID. No 6, mentioned in example 1. The activity found is shown below:

$TEAC_{YAEERYPIL}$(1 MINUTE)=0.8

$TEAC_{YAEERYPIL}$(6 MINUTES)=1.2

$TEAC_{YAEERYPIL}$(10 MINUTES)=1.3

The results therefore show that 1 mg of YAEERYPIL (SEQ. ID. NO: 6) displays 1.3 times more antioxidant activity than 1 mg of 6-hydroxy-2,5,7,8-teramethylchroman-2-carboxylic acid.

Example 4

Obtaining of Bioactive Peptides Starting from Ovalbumin Hydrolysed with Pepsin at Atmospheric Pressure The hydrolysate was obtained using as ovalbumin grade VI as substrate (99% purity) (Sigma). The substrate was dissolved in water at a concentration of 100 mg/ml and the pH was adjusted to 2.0 adding 1N HCl. In this particular embodiment of the invention pepsin was added (E.C. 3.4.23.1 type A, 10000 U/mg of protein) coming from pig stomach (Sigma) at an enzyme/substrate ratio 1/100, w/w). The hydrolysis was conducted at a temperature of 37° C. for 3 hours, at atmospheric pressure (0.1 MPa). The deactivation of the pepsin was achieved by raising the pH to 7.0 with 1N NaOH.

The measurement of ACEI activity showed that unhydrolysed ovalbumin does not possess ACEI activity ($IC_{50}$>750 µg/ml) but it inhibits the enzyme after 3 hours of hydrolysis with pepsin ($IC_{50}$=129.0±0.6 µg/ml). The hydrolysate thus obtained was analysed by means of RP-HPLC-MS/MS. The following sequences at least were found: SEQ. ID. No 1, SEQ. ID. No 2, SEQ. ID. No 3, SEQ. ID. No 4, SEQ. ID. No 5, SEQ. ID. No 6, SEQ. ID. No 7 and SEQ. ID. No 8. Among them the sequences SEQ. ID. No 2, SEQ. ID. No 3, SEQ. ID. No 5 and SEQ. ID. No 6 possess $IC_{50}$ less than 34 µM (example 2). SEQ. ID. No 2, SEQ. ID. No 3 and SEQ. ID. No 6 also display anti-hypertensive activity in rats (example 2) and SEQ. ID. No 6 possesses antioxidant activity towards free radicals (example 3).

Example 5

Obtaining of Bioactive Peptides Starting from Ovalbumin Hydrolysed with Pepsin Under High Hydrostatic Pressure The hydrolysate was obtained using ovalbumin grade VI as substrate (99% purity) (Sigma). As enzyme, pepsin was added (E.C. 3.4.23.1 type A, 10000 U/mg of protein) coming from pig stomach (Sigma). The substrate was dissolved in water at a concentration of 2 mg/ml and the pH was adjusted to 2.0 adding 1N HCl. Pepsin was added (enzyme/substrate ratio 1/20, w/w). The hydrolysis was conducted at a temperature of 37° C. for 30 minutes, at different hydrostatic pressures (100, 200, 300 and 400 MPa). The deactivation of the pepsin was achieved by raising the pH to 7.0 with 1N NaOH.

The treatments with high pressure were conducted in discontinuous hydrostatic pressure equipment (900 HP Eurotherm Automation) with capacity for 2350 ml, which reaches a pressure of 500 MPa. The high pressure chamber consists of a stainless steel cylinder filled with pressure transmitter medium (water) inside which the mixture of substrate and enzyme is introduced, enclosed in an Eppendorf plastic tube without leaving any air chamber. The equipment reaches the desired pressure at a speed of 2.5 MPa/second and, following treatment, is brought back down to zero at the same speed. The equipment is accompanied by an auxiliary bath which, by means of the circulation of water through an exterior jacket surrounding the cylinder, permits treatment at temperatures from −20° C. to 95° C. The temperature of the process is controlled by means of a thermocouple submerged in the pressure transmitter medium.

The hydrolysates thus obtained were analysed by means of RP-HPLC-MS/MS. The following sequences at least were found: SEQ. ID. No 3, SEQ. ID. No 5 and SEQ. ID. No 6 which, as stated in example 2, possess $IC_{50}$ less than 7 µM. SEQ. ID. No 3 and SEQ. ID. No 6 also display anti-hypertensive activity in rats (example 2) and SEQ. ID. No 6 possesses antioxidant activity towards free radicals (example 3). This example shows how the use of high hydrostatic pressure permits hydrolysates containing active peptides to be obtained faster than when carrying out the hydrolysis at atmospheric pressure. It can be highlighted that, under these conditions, SEQ. ID. No 2 was not obtained, which could have an impact on the industrial applicability of the hydrolysates.

The invention claimed is:

1. An isolated bioactive product wherein said product:
   a) is an isolated peptide sequence selected from the group consisting of SEQ ID NO: 1, SEQ ID NO: 4, SEQ ID NO: 6, SEQ ID NO: 7, and SEQ ID NO: 8;
   b) has a molecular weight between 365.2 and 1152.58 Da;
   c) is obtained from the amino acid positions 36-126 of the amino acid sequence of ovalbumin or is synthesized by solid phase peptide synthesis; and
   d) possesses ACEI activity in vitro and/or possesses antihypertensive activity in spontaneous hypertensive rats in vivo.

2. The isolated bioactive product according to claim 1 wherein said product obtained from the amino acid sequence of ovalbumin is obtained by means of recombinant methods.

3. The isolated bioactive product according to claim 1 wherein said product is obtained by a method comprising:
   a) obtaining from an animal or from a microorganism a substrate containing ovalbumin;
   b) contacting the substrate containing ovalbumin with pepsin at pH 2.0-3.0, for a period of time between 10 minutes and 24 hours, and a temperature sufficient to enzymatically hydrolyze the ovalbumin, thereby obtaining a hydrolysate, wherein said hydrolysate contains a peptide selected from the group consisting of SEQ ID NO: 1, SEQ ID NO: 4, SEQ ID NO: 6, SEQ ID NO: 7, and SEQ ID NO: 8;
   c) dissolving or dispersing the hydrolysate in water or buffer solution; and
   d) isolating from the dissolved or dispersed hydrolysate of step (c) a peptide from the group consisting of SEQ ID NO: 1, SEQ ID NO: 4, SEQ ID NO: 6, SEQ ID NO: 7, and SEQ ID NO: 8.

4. The isolated bioactive product according to claim 3 wherein the substrate containing ovalbumin defined in step (a) of claim 3 is selected from the group consisting of pure ovalbumin, egg white, and ovoproducts intended for the catering and restaurant trade, for dietary complements for sportsmen, or for animal food.

5. The isolated bioactive product according to claim 3 wherein the period of time defined in step (b) of claim 5 is less than 3 hours.

6. A composition consisting essentially of the isolated peptide sequence according to claim 1 and pharmaceutically acceptable salts thereof, the peptide sequence selected from the group consisting of SEQ ID NO: 1, SEQ ID NO: 4, SEQ ID NO: 6, SEQ ID NO: 7, and SEQ ID NO: 8.

* * * * *

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<221> NAME/KEY: SOURCE
<222> LOCATION: 1..5
<223> OTHER INFORMATION: /mol_type="protein"
      /note="synthetic"
      /organism="Artificial Sequence"
```

```
<400> SEQUENCE: 1

Tyr Gln Ile Gly Leu
1               5

<210> SEQ ID NO 2
<211> LENGTH: 3
<212> TYPE: PRT
<213> ORGANISM: Artificial Sequence
<220> FEATURE:
<221> NAME/KEY: SOURCE
<222> LOCATION: 1..3
<223> OTHER INFORMATION: /mol_type="protein"
      /note="synthetic"
      /organism="Artificial Sequence"

<400> SEQUENCE: 2

Ile Val Phe
1

<210> SEQ ID NO 3
<211> LENGTH: 7
<212> TYPE: PRT
<213> ORGANISM: Artificial Sequence
<220> FEATURE:
<221> NAME/KEY: SOURCE
<222> LOCATION: 1..7
<223> OTHER INFORMATION: /mol_type="protein"
      /note="synthetic"
      /organism="Artificial Sequence"

<400> SEQUENCE: 3

Arg Ala Asp His Pro Phe Leu
1               5

<210> SEQ ID NO 4
<211> LENGTH: 3
<212> TYPE: PRT
<213> ORGANISM: Artificial Sequence
<220> FEATURE:
<221> NAME/KEY: SOURCE
<222> LOCATION: 1..3
<223> OTHER INFORMATION: /mol_type="protein"
      /note="synthetic"
      /organism="Artificial Sequence"

<400> SEQUENCE: 4

Phe Ser Leu
1

<210> SEQ ID NO 5
<211> LENGTH: 8
<212> TYPE: PRT
<213> ORGANISM: Artificial Sequence
<220> FEATURE:
<221> NAME/KEY: SOURCE
<222> LOCATION: 1..8
<223> OTHER INFORMATION: /mol_type="protein"
      /note="synthetic"
      /organism="Artificial Sequence"

<400> SEQUENCE: 5

Phe Arg Ala Asp His Pro Leu Phe
1               5

<210> SEQ ID NO 6
<211> LENGTH: 9
<212> TYPE: PRT
<213> ORGANISM: Artificial Sequence
<220> FEATURE:
<221> NAME/KEY: SOURCE
```

```
<222> LOCATION: 1..9
<223> OTHER INFORMATION: /mol_type="protein"
      /note="synthetic"
      /organism="Artificial Sequence"

<400> SEQUENCE: 6

Tyr Ala Glu Glu Arg Tyr Pro Ile Leu
1               5

<210> SEQ ID NO 7
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="synthetic"
      /organism="Artificial Sequence"

<400> SEQUENCE: 7

Arg Asp Ile Leu Asn Gln
1               5

<210> SEQ ID NO 8
<211> LENGTH: 5
<212> TYPE: PRT
<213> ORGANISM: Artificial Sequence
<220> FEATURE:
<221> NAME/KEY: SOURCE
<222> LOCATION: 1..5
<223> OTHER INFORMATION: /mol_type="protein"
      /note="synthetic"
      /organism="Artificial Sequence"

<400> SEQUENCE: 8

Ser Ala Leu Ala Met
1               5

<210> SEQ ID NO 9
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="synthetic"
      /organism="Artificial Sequence"

<400> SEQUENCE: 9

Arg Ala Asp His Pro Phe
1               5

<210> SEQ ID NO 10
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="synthetic"
      /organism="Artificial Sequence"

<400> SEQUENCE: 10

Arg Pro Phe His Pro Phe
1               5

<210> SEQ ID NO 11
```

```
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="synthetic"
      /organism="Artificial Sequence"

<400> SEQUENCE: 11

Arg Pro Leu Lys Pro Trp
1               5

<210> SEQ ID NO 12
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="synthetic"
      /organism="Artificial Sequence"

<400> SEQUENCE: 12

Glu Ser Ile Ile Asn Phe
1               5

<210> SEQ ID NO 13
<211> LENGTH: 10
<212> TYPE: PRT
<213> ORGANISM: Artificial Sequence
<220> FEATURE:
<221> NAME/KEY: SOURCE
<222> LOCATION: 1..10
<223> OTHER INFORMATION: /mol_type="protein"
      /note="synthetic"
      /organism="Artificial Sequence"

<400> SEQUENCE: 13

Val Leu Leu Pro Asp Glu Val Ser Gly Leu
1               5                   10

<210> SEQ ID NO 14
<211> LENGTH: 4
<212> TYPE: PRT
<213> ORGANISM: Artificial Sequence
<220> FEATURE:
<221> NAME/KEY: SOURCE
<222> LOCATION: 1..4
<223> OTHER INFORMATION: /mol_type="protein"
      /note="synthetic"
      /organism="Artificial Sequence"

<400> SEQUENCE: 14

Glu Leu Ile Asn
1

<210> SEQ ID NO 15
<211> LENGTH: 10
<212> TYPE: PRT
<213> ORGANISM: Artificial Sequence
<220> FEATURE:
<221> NAME/KEY: SOURCE
<222> LOCATION: 1..10
<223> OTHER INFORMATION: /mol_type="protein"
      /note="synthetic"
      /organism="Artificial Sequence"
```

```
<400> SEQUENCE: 15

Tyr Arg Gly Gly Leu Glu Pro Ile Asn Phe
1               5                   10
```